(12) United States Patent
Fuertes

(10) Patent No.: US 7,674,381 B2
(45) Date of Patent: Mar. 9, 2010

(54) METHOD FOR PREPARING L-IDITOL

(75) Inventor: Patrick Fuertes, Lomme (FR)

(73) Assignee: Roquette Freres, Lestrem (FR)

( * ) Notice: Subject to any disclaimer, the term of this patent is extended or adjusted under 35 U.S.C. 154(b) by 1051 days.

(21) Appl. No.: 11/250,576

(22) Filed: Oct. 17, 2005

(65) Prior Publication Data

US 2006/0096588 A1    May 11, 2006

(30) Foreign Application Priority Data

Oct. 15, 2004    (FR)    ................................ 04 10973

(51) Int. Cl.
*B01D 15/08*    (2006.01)
(52) U.S. Cl. .................. 210/635; 210/656; 210/659; 127/46.1; 127/46.2; 127/46.3; 435/72; 536/127
(58) Field of Classification Search ................ 210/656, 210/635, 659, 198.2; 127/46.1, 46.2, 46.3; 435/72; 536/127
See application file for complete search history.

(56) References Cited

U.S. PATENT DOCUMENTS

| | | | |
|---|---|---|---|
| 2,985,589 A | 5/1961 | Broughton et al. | |
| 3,268,605 A | 8/1966 | Boyd | |
| 3,291,726 A | 12/1966 | Broughton | |
| 4,096,036 A * | 6/1978 | Liu et al. | .................. 435/94 |
| 4,422,881 A | 12/1983 | Devos et al. | |
| 2004/0143024 A1* | 7/2004 | Yoshino et al. | ............. 514/738 |

OTHER PUBLICATIONS

V. Vongsuvanlert et al. "L-Iditol production from L-sorbose by a methanol yeast, *Candida boidinii* No. 2201", Journal of Fermentation Technology, vol. 66, n° 5, 1988, pp. 517-523, XP002331358, Tokyo, JP.
M. Ogawa et al., "Microbial Production of Optically Pure L-iditol by yeast strains", Applied and Environmental Microbiology, vol. 46, n° 4, Oct. 1983, pp. 912-916, XP008047444, American Society for Microbiology, Washington, DC, USA.
E.I. Fulmer et al., "The Effect of the Concentration of Sorbitol upon the Production of Sorbose by the Action of Acetobacter suboxydans", Journal of the American Chemical Society, vol. 58, n° 6, Jun. 1936, pp. 1012-1013, XP002331486, American Chemical Society, Washington, DC, USA.

(Continued)

*Primary Examiner*—Ernest G Therkorn
(74) *Attorney, Agent, or Firm*—Young & Thompson

(57) ABSTRACT

Method for preparing highly pure L-iditol, consisting in subjecting a mixture of L-iditol and of L-sorbose to a chromatographic treatment, in such a way as to obtain at least two fractions, one of which is highly enriched in L-iditol and the other of which is highly enriched in L-sorbose.

10 Claims, 2 Drawing Sheets

Scheme 1

OTHER PUBLICATIONS

Y. Khouvine "Réduction de l'alpha-d-glucoheptulose par le nickel de Raney", Comptes-Rendus Hebdomadaires des Séances de l'Académie des Sciences, vol. 204, 1937, pp. 983-984, XP002331485, Gauthier-Villars, Montreuil, FR.

J.F. Ruddlesden et al. "Diastereoselective Control in Ketose Hydrogenation with Supported Copper and Nickel Catalysts", Faraday Discussions of the Chemical Society, 1981, vol. 72, pp. 397-411.

M. G. Bertrand entitled Sur la Synthèse et la nature chimique de la Sorbiérite, Bull. Soc. Chim. (3) 33, 1905, p. 264-267.

Wright et al., "Catalytic Isomerization of the Hexitols D-Glucitol, D-Mannitol, L-Iditol, and Galactitol", Journal of Organic Chemistry, vol. 26 May 1961, pp. 1588-1596.

* cited by examiner

Scheme 1

Scheme 2

METHOD FOR PREPARING L-IDITOL

The invention relates to a method for preparing highly pure L-iditol.

L-Iditol is a sweetly flavoured hexitol which could find applications in the food industry if it happened to be possible to produce it in large amounts and at low cost, or could prove to be a synthesis intermediate for the preparation of other products, and in particular of products of internal anhydride formation, such as iditan and especially isoidide or 1,4,3,6-dianhydroiditol.

These anhydrides, of which the hydroxyl groups, and in particular the two —(OH) groups of the isoidide, very readily undergo etherification or esterification reactions, in turn become advantageous intermediates although they can also find applications as such for example as osmotic agents or water-retaining agents in particular.

Esterification of the isoidide with monocarboxylic acids makes it possible to obtain diesters, which can be used as plasticizers in synthetic resins. The diethers, such as dimethyl isoidide, prove to be excellent solvents for certain pharmaceutical active agents or else for certain natural or synthetic polymers.

Isoidide can also itself constitute one of the monomeric units of polyesters, in connection with diacids and other bivalent alcohols.

By analogy with the hydrogenation of D-glucose, which gives D-sorbitol with an almost total yield, L-iditol could be obtained with a virtually stoichiometric yield by hydrogenation of L-idose. L-Idose is not, however, a carbohydrate that is found naturally and its extraction from plant sources, for example, cannot therefore be envisaged.

L-Iditol, formerly called sorbieritol, exists in a small amount in the juice of sorbs (fruit of the service tree), along with small amounts of sorbitol (D-glucitol). Here again, extraction from these berries cannot be envisaged industrially.

It is known that the catalytic hydrogenation of ketoses results in two stereoisomers. Thus, the hydrogenation of L-sorbose makes it possible to obtain a mixture of D-sorbitol and its C5 epimer, L-iditol.

The use of certain catalysts and/or the use of specific hydrogenation conditions make it possible to vary, within certain limits, the proportions of the two enantiomers. The document "Diastereoselectivity control in ketose hydrogenations with supported copper and nickel catalysts" by J. F. Ruddlesden et al., published in 1981, indicates for example that a copper-based catalyst makes it possible to obtain, by hydrogenating L-sorbose, 68% of D-glucitol (D-sorbitol) and that a nickel-based catalyst makes it possible to obtain predominantly the other enantiomer, i.e. 64% of L-iditol.

The isomerization of readily available hexitols such as sorbitol or mannitol also makes it possible to form iditol, although in minor amounts. The document "Catalytic isomerisation of the hexitols; D-glucitol, D-mannitol, L-iditol and galactitol" by L. Wright and L. Hartman, Journal of Organic Chemistry, Vol. 26, May 1961, indicates that, at 170° C. and under a hydrogen pressure of 1900 p.s.i. (130 bar) and in the presence of a nickel catalyst, an equilibrium is obtained for a system containing 50% of sorbitol, 25% of mannitol and 25% of iditol.

These two methods, ketose hydrogenation and hexitol isomerization, therefore give D-iditol in noticeable amounts, but unfortunately with poor purity and a poor yield due to the appearance or the persistence in the reaction medium of other polyols.

The extraction of D-iditol from these reaction mixtures therefore proves to be very complex and it is generally carried out by forming chemical addition compounds of these various polyols (benzoic aldehyde, acetic anhydride) and/or crystallizations in an organic solvent phase, pyridine, alcohol, etc, of these compounds or polyols.

Biological methods of reduction of L-sorbose virtually exclusively to L-iditol are known and make it possible to obtain products that are highly rich in L-iditol. However, they have never been used industrially, either because they operate with poor yields, or their use proves to be impossible or too difficult on this scale.

The document "Microbial production of optically pure L-iditol by yeast strains", Appl. Environ. Microb. Vol. 46, No. 4, pp. 912-916, 1983" teaches that *Candida intermedia* makes it possible to obtain 50 g/l of L-iditol from 150 g/l of L-sorbose in 5 days. Although there is no more L-sorbose remaining in the culture must at the end of fermentation, direct crystallization of the L-iditol has been found to be impossible, even after demineralization. The authors had to go via the hexaacetate and crystallization from methanol in order to obtain crystals melting at between 70 and 73° C.

The document "L-iditol production from L-sorbose by a methanol yeast, *Candida boidinii* (Kloeckera sp.) No. 2201", J. Ferment. Technol., Vol. 66, No. 5, pp. 517-523, 1988, describes a purely enzymatic method of reduction of L-sorbose to L-iditol using D-sorbitol dehydrogenase and immobilized *C. boidinii* cells as an NADH support, the regeneration of which is provided by a set of enzymes for oxidizing methanol, this methanol constituting the hydrogen source that provides this regeneration. The conversion yield is established at approximately 96% in about forty hours for a concentration in the region of 150 g/l. No mention is made of how the L-iditol can be isolated from the reaction medium. This extremely complex and delicate method has never been used on an industrial scale.

Consequently, the search is still on for a method suitable for abundantly providing L-iditol with a yield and a purity that are sufficiently high for industrial companies to be able to have this hexitol available to them in an abundant amount and under advantageous cost conditions.

It is to this problem, that has been posed for a great many years, that the applicant company has to its credit provided a solution by finding that it is possible to obtain L-iditol in a highly pure state and under entirely advantageous economical conditions by carrying out chromatographic fractionation of a mixture of L-sorbose and L-iditol on cationic resins or zeolites, cationic resins been preferred and consisting of those which are used for the chromatographic separation of sugars such as glucose and fructose or of polyols such as sorbitol and mannitol.

The applicant company has in fact noted, after many trials, that the chromatographic separation of L-sorbose and of L-iditol occurs much more readily than the chromatographic separation of L-iditol and of D-sorbitol, which, a priori would provide a much simpler method.

The mixtures of L-sorbose and of L-iditol, the first of which were obtained by the French chemist Gabriel Bertrand at the beginning of the last century (G. Bertrand, Bull. Soc. Chim., 3rd series, 1905, t. 33, p. 166 and seq. p. 264-267), can be obtained as indicated by Bertrand, by acid hydrogenation of the L-sorbose and then bacterial oxidation of the D-sorbitol/L-iditol mixture obtained by means of this hydrogenation.

These mixtures can also result from a more selective hydrogenation of sorbose, orienting the latter towards an increased production of L-iditol (J. F. Ruddlesden), and then bacterial oxidation of this mixture.

They may also result from a process of hexitol isomerization. In this case, the presence of mannitol will, after the bacterial oxidation, result in the corresponding appearance of fructose, that it will be advisable to recover at the same time as the L-sorbose during the chromatography step in order to separate these two ketoses from the L-iditol.

Of course, the various ways of obtaining mixtures containing L-iditol and of oxidizing them can be combined, mixtures that do not contain any mannitol and fructose or that contain only a small amount of mannitol and fructose being, however, more acceptable to the invention.

Advantageously, the chromatographic fractions that contain the oxidation product(s), i.e. essentially the L-sorbose but also optionally fructose, are again hydrogenated, alone or in the presence of newly used L-sorbose. These fractions are then again subjected to bacterial oxidation. This manner of carrying out the procedure makes it possible to virtually exclusively obtain L-iditol from the L-sorbose, and with a stoichiometric yield approaching one.

It is recalled here that the hydrogenation of fructose generates the two C2 epimeric hexitols, namely D-sorbitol and D-mannitol, and that, when the sorbose fraction derived from the chromatography also contains fructose, this gives, after hydrogenation, a ternary composition corresponding to the hexitol isomerization products and containing D-sorbitol, D-mannitol and L-iditol.

Also recalled here in move recent terms is Bertrand's rule that the latter had established by studying the action of *Bacterium xylinum* (*Acetobacter*) on a series of polyols and in particular on those contained in sorb juices: "The sorbose bacterium carries out a stereospecific dehydrogenation with respect to the secondary alcohol function in the region of the primary alcohol function when the two hydroxyls closest to the primary alcohol are in the cis position". This bacterium, by means of the broad-spectrum dehydrogenases that it synthesizes, is thus capable of oxidizing glycerol to dihydroxyacetone and erythritol to erythrulose, but also xylitol to xylulose, sorbitol to sorbose and mannitol to fructose, this list not being exhaustive.

It ensues that the method of preparing highly pure L-iditol in accordance with the invention is characterized in that a syrup of a mixture of L-iditol and L-sorbose is subjected to a chromatographic treatment resulting in at least two fractions being obtained, one of which is highly enriched in L-iditol (fraction X1) and the other of which is highly enriched in L-sorbose (fraction X2).

Advantageously, the chromatographic treatment is carried out in such a way that the fraction highly enriched in L-iditol (fraction X1) is composed, the percentages being expressed by weight with respect to solids:

of from 80 to 99.9%,
preferably of from 90 to 99.5%, and even more preferably of from 95 to 99.5% of L-iditol, The remainder up to 100% essentially consisting of L-sorbose.

According to an advantageous embodiment of the method of the invention, the mixture of L-iditol and L-sorbose is obtained by fermentation of a solution of D-sorbitol and of L-iditol using a microorganism that produces dehydrogenases of the *acetobacter* or *gluconobacter* genus, able to convert D-sorbitol to L-sorbose.

According to another advantageous embodiment of the method of the invention, the solution of D-sorbitol and of L-iditol subjected to fermentation is obtained by catalytic hydrogenation of L-sorbose.

According to another more particularly advantageous embodiment of the method of the invention, the fraction X2 highly enriched in L-sorbose is collected so as to be mixed with the L-sorbose intended for the catalytic hydrogenation.

L-Sorbose is a ketose produced on a scale of several tens of thousands of tonnes per year worldwide since it is an intermediate in the synthesis of ascorbic acid or vitamin C. It is itself obtained by fermentation of a solution of pure D-sorbitol, most commonly using the same microorganisms that are used to ferment the mixtures of D-sorbitol and of L-iditol in the method of the present invention.

Pure D-sorbitol is produced worldwide on a scale of several hundred thousand tonnes per year and it is obtained by hydrogenation of highly rich D-glucose solutions. This hydrogenation can be carried out using the same catalysts that are used to hydrogenate the L-sorbose solutions.

Another remarkable aspect of the invention is therefore that it makes it possible to use common materials: reactors and fermenters, both for obtaining L-sorbose and for obtaining the mixtures of L-sorbose and of L-iditol to be chromatographed. The catalysts to be used: on the one hand metal catalysts for the hydrogenation and, on the other hand biological catalysts for the fermentation, are also the same. When implementing the method of the invention, it is therefore particularly advantageous to combine the steps leading from D-glucose to L-iditol on the same site.

DESCRIPTION OF THE PREFERRED EMBODIMENTS

Figure 1:
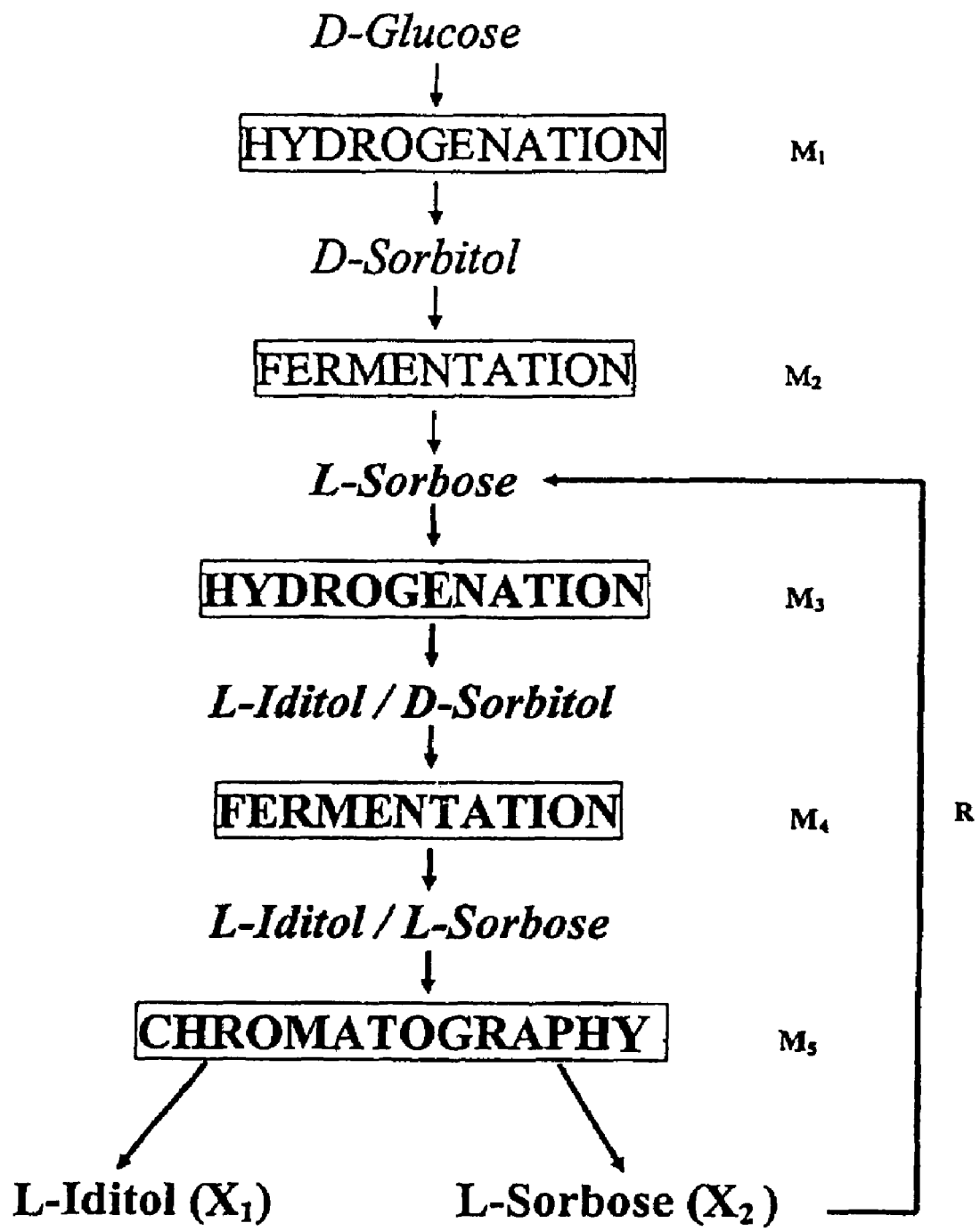
FIG. 1 shows the steps leading from D-glucose to L-iditol.

Reference will be made with interest to the attached scheme 1, which reiterates in their entirety the steps leading from D-glucose to L-iditol, those that are more particularly claimed appearing in thicker letters and lines.

The invention will be understood even more clearly from the more detailed description that follows, from the illustrative but nonlimiting example and also from the attached schemes, said further description, example and schemes relating only to one advantageous embodiment.

In the abovementioned scheme 1, steps M1 and M2 correspond, respectively, to the hydrogenation of D-glucose to D-sorbitol and then to the conversion, via the fermentation pathway, of D-sorbitol to L-sorbose. These steps will not be given in further detail since they have already been sufficiently described in the literature such that anyone skilled in the art can implement them without difficulty. They could in any case be implemented under the conditions described below for steps M3 and M4.

Step M3 corresponds to the hydrogenation of L-sorbose to a mixture of D-sorbitol and of L-iditol. It can be carried out under the conditions described in the article by J. F. Ruddlesden and leading to an enantiomeric excess of L-iditol (64%, see Table 5). It can also be carried out using a ruthenium or Raney nickel catalyst, continuously or batchwise. When batchwise hydrogenation is used, it is preferred to work in the presence of approximately 5 to 10% of Raney nickel with a sorbose concentration of between 300 and 450 g of sugar per kilogram of solution and at a temperature of between 80 and 130° C. In order to prevent the appearance of hexitol isomerization products, it is preferred to maintain the pH at a value below 8.0. The hydrogen pressure is maintained at between 20 and 80 bar until the content of reducing sugars in the hydrogenated mixture becomes less than 1%, and preferably less than 0.1%. The conventional sub-steps of purification of any hydrogenated syrup then follow, i.e. those of separation by settling out and then of filtration of the catalyst and those of purification of the soluble impurities by decoloration with animal black or on granular carbon and demineralization on cationic and anionic ion exchange resins, operating respectively in the hydrogen and hydroxyl cycle.

Step M4 corresponds to the oxidation of the mixture of D-sorbitol and of L-iditol caused by the bacterial dehydrogenases. During the corresponding fermentation, the sorbitol whose secondary alcohol function located in the C5-position obeys Bertrand's law is oxidized to a ketone function. The D-sorbitol therefore becomes L-sorbose. The L-iditol, none of the four secondary alcohol functions of which satisfies these conditions, remains unchanged during the fermentation.

For the fermentation of this mixture, use may be made of a culture medium having the following composition:

| | |
|---|---|
| Mixture of D-sorbitol and of L-iditol: | 100 to 200 g/l |
| Organic nitrogen (in the form of corn-steep or of yeast extract) | 2 g/l (yeast extract) |
| $KH_2PO_4$ | 1 to 3 g/l |
| $MgSO_4.7H_2O$ | 1 to 2 g/l | and which is introduced into a fermenter, sterilized and then inoculated with approximately 10% of a 20-hour preculture of a microorganism of the *Acetobacter* or *Gluconobacter* microorganism, for example *Gluconobacter oxydans*.

The fermentation is continued at a temperature of 25 to 35° C. with aeration corresponding to 1 to 1.5 volumes of air per volume of culture and per minute, at a pH of 4.0 to 6.0 and for a period of time generally between 24 and 48 hours, at the end of which all the D-sorbitol has been converted to L-sorbose.

This fermentation can then be purified in a known manner by filtration or centrifugation, decoloration with animal black or on granular carbon and then demineralization on cationic and anionic resin operating, respectively, in the hydrogen and hydroxyl cycle. This purified syrup is then concentrated in order to be subjected to chromatography step M5.

This chromatographic fractionation step M5 can be carried out in any known manner, batchwise or continuously (SMB, simulated moving bed; ISMB, improved simulated moving bed; SSMB, sequential simulated moving bed, etc) on strongly acidic cationic resin type adsorbents, preferably loaded with alkali metal or alkaline earth metal ions, or on cationic zeolite type absorbents, also loaded with the same ions.

Examples of such methods of chromatographic separation are given, for example, in U.S. Pat. Nos. 2,985,589, 3,291,726 and 3,268,605 from the company U.O.P.

According to a preferred embodiment, the chromatographic separation step is carried out by using the method and the equipment described in U.S. Pat. No. 4,422,881 and its corresponding French patent FR 2,454,830, of which the applicant company is the proprietor.

Whatever the method of chromatographic separation selected, use is made, as adsorbent, of a cationic material, preferably of a strong cationic resin, of the sulphonated polystyrene type, this resin being even more preferably used in ionic calcium form and being crosslinked with divinylbenzene to a degree of approximately 4 to 10%.

The choice of the parameters of the chromatography step, including in particular:
    the elution flow rate,
    the flow rate of supplied syrup of the L-sorbose/L-iditol mixture,
    the flow rate of extraction of the fraction X1 enriched in L-iditol,
    the composition of the desorption, adsorption and enrichment zones, is illustrated in the example.

This choice is made such that the fraction X1, which is highly adsorbed by the resin, exhibits a richness in terms of L-iditol, the percentages being expressed by weight of solids:
    from 80 to 99.9%,
    preferably from 90 to 99.5%, and even more preferably from 95 to 99.5%,
    the remainder up to 100% consisting essentially of L-sorbose.

In order to obtain these results, said parameters are chosen as follows, when the chromatography step is carried out using the method and the equipment described in U.S. Pat. No. 4,422,811 and when the adsorbent used is a cationic resin of small particle size, crosslinked with 7% of divinylbenzene (PCR732 from the company Purolite) and used in calcium form:
    elution flow rate from 375 to 450 l/h/m$^3$ of adsorbent,
    flow rate of supply of syrup of L-iditol/L-sorbose mixture from 30 to 45 1/h/m$^3$ of adsorbent,
    flow rate of extraction of the fraction enriched in L-iditol from 100 to 140 /h/m$^3$ of adsorbent.

The chromatography step results, moreover, in the concomitant obtaining of a fraction X2, that is excluded from the resin and highly enriched in L-sorbose.

This fraction X2 highly enriched in L-sorbose is preferably recycled, in accordance with the invention, in the hydrogenation step, conveniently as a mixture with the fermentation musts derived from step M2 so as to benefit from a common purification. This recycling is symbolized by the letter "R" that appears to the right of the arrow symbolizing said recycling.

Preferably, this fraction X2 is composed, the percentages being expressed by weight with respect to solids:
    of 60 to 99.5% of L-sorbose,
    preferably of 80 to 99%, and even more preferably of 90 to 99% of L-sorbose,
    the remainder up to 100% consisting essentially of L-iditol.

The purity of this fraction X1 may be such that it is often possible to use it directly in the food sector or as a starting material in the production of derived products such as internal dehydration products, namely iditan or isoidide. However, this fraction X1, which constitutes the highly pure L-iditol obtained according to the method of the present invention, is particularly easy to crystallize. Simple concentration to a solids content of about 80%, preferably followed by cooling in a shaken tank, gives a lot of superb crystals., that are readily separated from their mother liquors by filter-drying. The use of organic solvents is not needed in order to carry out this crystallization. This manner of proceeding makes it possible to increase the richness of the L-iditol well beyond what it was in this fraction X1.

EXAMPLE

A mixture containing 45% of L-sorbose and 55% of L-iditol was subjected to chromatographic fractionation. In reality, this mixture contained a few traces of other sugars and polyols at a content of about 2%. This mixture had been obtained by fermenting, using *Gluconobacter oxydans* ATCC 19357, a mixture of D-sorbitol and of L-iditol obtained by hydrogenating a solution containing 40% of L-sorbose. This hydrogenation carried out using Raney nickel under substantially neutral pH conditions had provided a syrup containing 0.2% of residual reducing sugars and containing D-sorbitol and L-iditol in substantially equivalent amounts. After fermentation, this syrup had been purified by filtration and then decoloration on granular carbon and, finally, demineralization on ion exchange resins, before being concentrated to a solids content of 50%.

Figure 2:
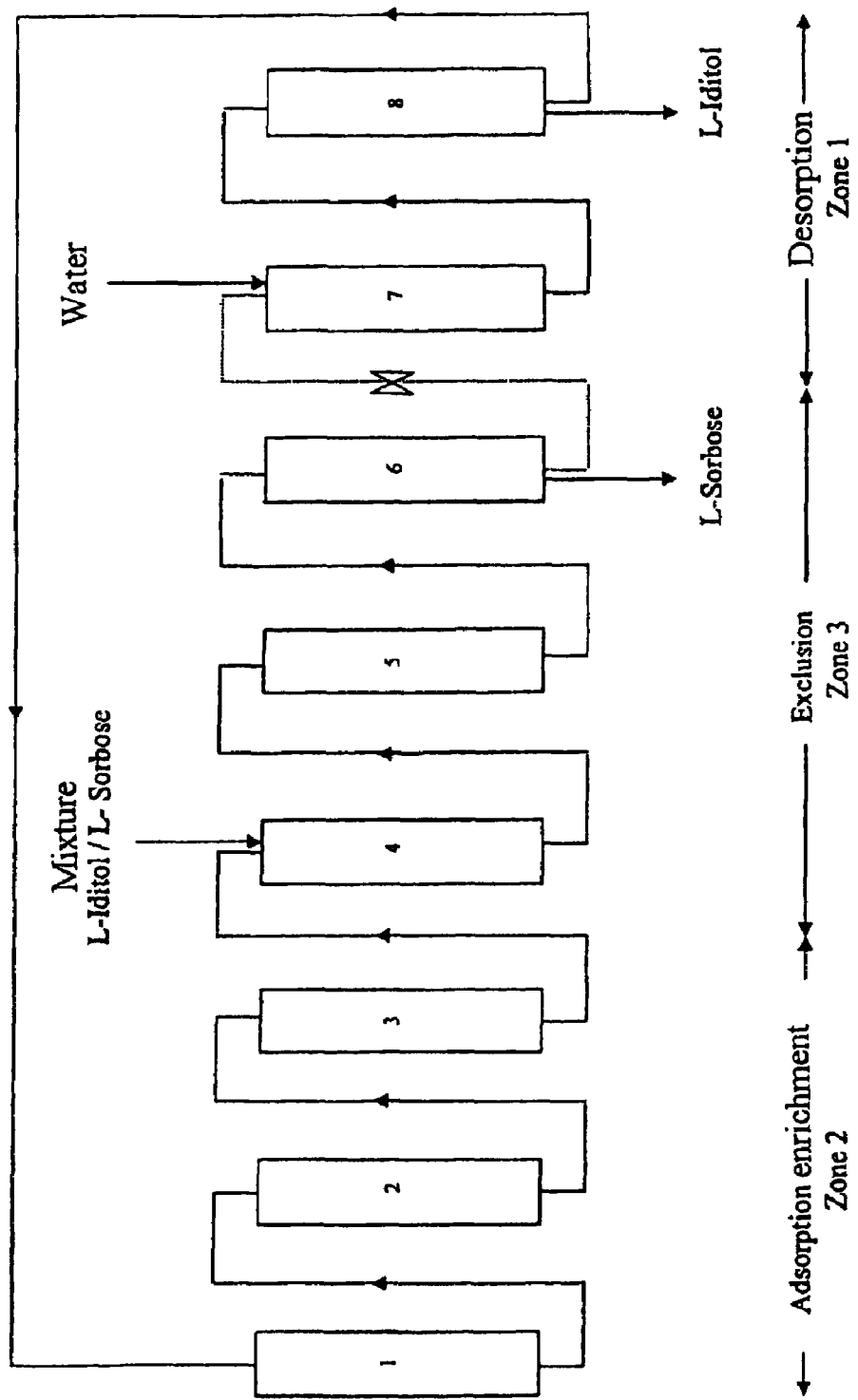
FIG. 2 shows use of a simulated moving bed to recover L-iditol.

The chromatographic installation comprises, as shown in FIG. 2 of American patent U.S. Pat. No. 4,422,881, the content of which is incorporated into the present description by way of reference, eight columns or stages each of 200 litres, provided with strong cationic resin type adsorbent in calcium form and having a fine and homogeneous particle size (0.2 to 0.3 mm) (PCR732 from Purolite).

In this installation, the openings and closings of the electrovalves creating the simulated moving bed are regulated so as to establish a two-stage L-iditol desorption zone I, a three-stage adsorption-enrichment zone II and a three-stage L-sorbose exclusion zone III, as shown on the present scheme 2, which is a simplified representation of FIG. 2 of U.S. Pat. No. 4,422,881 and on which have been shown only:
  columns C1 to C8,
  the closing device providing the direction of the chromatographic flow, in this instance the electrovalve located between columns 6 and 7,
  the piping for the L-iditol and L-sorbose syrup feed to be separated,
  the piping for the supply of water for elution providing the separation,
  the piping for the extraction of the fraction X1 enriched in L-iditol appearing on column 8,
  the piping for the extraction of the fraction X2 enriched in L-sorbose appearing on column 6.

The closing device maintains, in the adopted configuration, a complete leak-tightness between, on the one hand, the zone III, which is an exclusion zone at the end of which the L-sorbose is recovered, and, on the other hand, the L-iditol desorption zone I, at the head of which the desorption water is introduced.

A timing device ensures, for a certain period of time and for the flow rates indicated hereinafter, a sufficient supply of desorption water at the first stage or first column of the zone I (column 7 on the present scheme 2) to carry out the desorption of all the L-iditol, and also a supply (column 4) of a volume of the mixture of L-iditol and of L-sorbose to be separated that is compatible with the volume of adsorbent contained in the column and its adsorption capacity, so as to obtain a degree of extraction of the L-sorbose at least equal to 80% of the L-sorbose present in the mixture to be separated, at a richness at least equal to 60% with respect to sorbose.

These conditions being satisfied, the timing device brings about the one-stage shift to the right, on the FIG. 2, of opening and closing of all the electrovalves. Eight shifts or cycles must therefore be performed in order to obtain the state represented in this FIG. 2.

The abovementioned extraction rate and purities are kept constant by adjusting the flow rate of the extraction pump (not shown) for extracting the L-iditol adsorbed (column 8). The exiting of the excluded L-sorbose fraction (column 6) takes place at atmospheric pressure and its constant flow rate results from the difference between the supply flow rate and the extraction flow rate. It is judicious to remove the portion of this fraction that consists only of water, at each beginning of a cycle.

The mixture of L-iditol and of L-sorbose that is introduced into the installation at the head of the exclusion zone III has, as indicated above, a solids content of about 50%. The temperature inside the separation columns is maintained at approximately 70° C.

The installation is operated under the following conditions:
  the timing device is regulated for a cycle time of 20 min,
  the mixture of L-iditol and of L-sorbose to be separated is conveyed to the installation at a flow rate of 60 litres/hour,
  the water eluent is conveyed to the installation at a flow rate of 660 litres/hour,
  the L-iditol fraction is extracted at a flow rate of 198 litres/hour,
  the L-sorbose fraction representing the remainder between the flow rates of the fluids entering the installation and those leaving it is therefore extracted spontaneously at a flow rate of 522 litres/hour. However, only the last 10 minutes of each cycle are conserved, since the preceding period corresponds to a fraction containing only virtually pure water, which is recovered for elution.

Tables 1 and 2 below summarize the conditions characterizing the operating of the chromatographic device.

TABLE 1

| Chromatographic entries | Syrup of L-iditol and L-sorbose | Water | Total |
|---|---|---|---|
| Flow rate l/h | 60 | 660 | 720 |
| Density kg/l | 1.192 | 1.000 | — |
| Solids content | 50% | 0 | 35.8 |
| Mass flow rate (kg/h) | 71.5 | 660 | 731.5 |
| Richness of L-iditol (% on a dry basis) | 55 | 0 | — |
| Mass flow rate of L-iditol (kg/h) | 19.7 | 0 | 19.7 |
| Mass flow rate of L-sorbose (kg/h) | 16.1 | 0 | 16.1 |

The effluents extracted from the installation are identified in Table 2.

TABLE 2

| Chromatographic exits | Fraction enriched in L-iditol (X1) | Fraction enriched in L-sorbose (X2) | Excess water | Total |
|---|---|---|---|---|
| Flow rate (l/h) | 198 | 261 | 261 | 720 |
| Density | 1.009 | 1.005 | 1.0 | — |
| Solids content (%) | 9.9 | 6.2 | <0.1 | 35.8 |
| Mass flow rate (kg/h) | 199.8 | 262.3 | | 462.1 |
| Richness of L-iditol (%) | 99.4 | <0.1 | | — |
| Mass flow rate of L-iditol (kg/h) | 19.7 | <0.1 | | 19.7 |
| L-Sorbose content (%) | <0.1 | 98.8 | | — |
| Mass flow rate of L-sorbose (kg/h) | <0.1 | 16.1 | | 16.1 |

This result corresponds to a L-iditol extraction yield of nearly 100%.

The fraction X2 enriched with L-sorbose was hydrogenated using the Raney nickel catalyst under a hydrogen pressure of 45 bar and at a temperature of 120° C. It provided a syrup that contained 54% of L-iditol and 46% of D-sorbitol.

It could have been hydrogenated under the same conditions in the presence of newly used L-sorbose.

Part of the fraction X1 containing, as indicated above, 99.4% of L-iditol was concentrated under vacuum to a solids content of 80% and was then cooled to a temperature of 25° C. in 24 hours with slow stirring. The crystalline mass was filter-dried and washed with a small amount of absolute ethanol. Crystalline L-iditol was obtained with a yield of 55% in a single crop. After drying in a fluidized bed, crystals with a water content of less than 1% and containing traces of ethanol were obtained. The purity of this L-iditol was more than 99.9%.

Another portion of this fraction X1 was concentrated to a solids content of 70% and 700 g of this syrup were placed in a round-bottomed laboratory evaporating flask of the Rotavapor trade mark. 0.1%, on a solids content basis, of 98% sulphuric acid was added thereto and this round-bottomed flask was maintained under vacuum in an oil bath heated to 150° C.

The progress of the reaction was followed by taking samples every 30 minutes for two and a half hours. The iditol, iditan and isoidide contents of the reaction medium were analysed by HPLC. The results are given in Table 3 below.

TABLE 3

| Time (h) | % Iditol | % Iditans | % Isoidide | % Others |
|---|---|---|---|---|
| 0 | 100 | 0 | 0 | 0 |
| 0.5 | 97.7 | 2.3 | 0 | 0 |
| 1.0 | 61.1 | 28.3 | 10.6 | 0 |
| 1.5 | 22.5 | 32.3 | 45.2 | 0 |
| 2.0 | 0.9 | 5.3 | 92.9 | 0.9 |
| 2.5 | 0 | 0 | 98.8 | 1.2 |

At the end of the reaction, the medium was diluted with its weight of water and the solution was treated with 2% of black for 1 hour at 70° C. The isoidide syrup was then demineralized on a mixed bed of ion exchange resins. The isoidide was then crystallized by concentrating the syrup to a solids content of 66.5% (refractometric estimation) and then cooling it with slow stirring, at a rate of 2° C./h. The crystals obtained were then filter-dried and washed with acetone.

A product having a moisture content of 10.9% and an iditan content of 0.4% was obtained. No isosorbide nor isomannide was detected.

The invention claimed is:

1. A method for preparing highly pure L-iditol, comprising the successive steps of:
   catalytically hydrogenating L-sorbose, which results in a solution of D-sorbitol and of L-iditol;
   fermenting the resulting solution of D-sorbitol and of L-iditol by using a microorganism that produces dehydrogenases of the *Acetobactor* or *Gluconbacter* genus, able to convert D-sorbitol to L-sorbose, so as to obtain a syrup of a mixture of L-iditol and of L-sorbose; and
   subjecting the resulting syrup of a mixture of L-iditol and of L-sorbose to a chromatographic treatment resulting in at least two fractions being obtained, one of which is highly enriched in L-iditol (fraction X1) and the other of which is highly enriched in L-sorbose (fraction X2).

2. The method for preparing highly pure L-iditol according to claim 1, wherein the chromatographic treatment is carried out in such a way that the fraction highly enriched in L-iditol (fraction X1) is composed of from 80 to 99.9% of L-iditol, the remainder up to 100% consisting essentially of L-sorbose.

3. The method for preparing highly pure L-iditol according to claim 2, wherein the fraction highly enriched in L-iditol (fraction X1) is composed of from 90 to 99.5% of L-iditol, the remainder up to 100% consisting essentially of L-sorbose.

4. The method for preparing highly pure L-iditol according to claim 3, wherein the fraction highly enriched in L-iditol (fraction X1) is composed of from 95 to 99.5% of L-iditol, the remainder up to 100% consisting essentially of L-sorbose.

5. The method for preparing highly pure L-iditol according to claim 1, wherein the fraction highly enriched in L-sorbose (fraction X 2) is collected and then mixed with the L-sorbose intended for the catalytic hydrogenation.

6. The method for preparing highly pure L-iditol according to claim 1, wherein the chromatographic treatment is carried out continuously.

7. The method according claim 6, wherein the chromatographic treatment is carried out using strong cationic resins loaded with alkali metal or alkaline earth metal ions.

8. The method according to claim 7, wherein the alkaline earth metal ions are calcium.

9. The method according to claim 1, wherein the fraction X1 is used to obtain, by concentration, L-iditol crystals.

10. The method according to claim 1, wherein the fraction X1 is used, without crystallizing the L-iditol therein, for the production of isoidide.

* * * * *